United States Patent [19]

Sircar et al.

[11] Patent Number: 4,952,693

[45] Date of Patent: Aug. 28, 1990

[54] OXAZOLO-PYRIMIDINE DERIVATIVES

[75] Inventors: Jagadish C. Sircar; Garry W. Pinter, both of Ann Arbor, Mich.

[73] Assignee: Warner-Lambert Company, Morris Plains, N.J.

[21] Appl. No.: 132,386

[22] Filed: Dec. 15, 1987

Related U.S. Application Data

[60] Division of Ser. No. 767,202, Aug. 22, 1985, Continuation-in-part of Ser. No. 660,152, Oct. 12, 1984, abandoned.

[51] Int. Cl.$^5$ ............................................. C07D 239/00
[52] U.S. Cl. .................................... 544/255; 544/276; 544/277
[58] Field of Search ................................ 544/255, 320

[56] References Cited

U.S. PATENT DOCUMENTS 4,411,690 10/1983 Tseng .................................. 544/255

FOREIGN PATENT DOCUMENTS 557466 5/1958 Canada .

OTHER PUBLICATIONS

D. S. Shewach et al., "Potentiation of 2'-deoxyguanosine cytotoxicity by a novel inhibitor of purine nucleoside phosphorylase, 8-amino-9-benzylguanine", Cancer Research 46, 519-523 (Feb. 1986).
Discussion at 16th Annual Graduate Student Meeting in Med. Chem. at U. of M., Ann Arbor, MI, "8 Amino-9-Benzylguanine".
Bio Chem. Pharm., 31, 163-171, (1982).
J. Am. Chem. Soc. 81, 3046-3051 (1959).
J. Het. Chem., 21, 1245-1246 (1984).
Heterocycles, vol. 22, No. 8, 1984, pp. 1789-1790.
Heterocycles, vol. 22, No. 11, 1984, pp. 2439-2441.

*Primary Examiner*—Nicholas S. Rizzo
*Attorney, Agent, or Firm*—Joan Thierstein

[57] ABSTRACT

Novel purine derivatives, particularly novel guanines and hypoxanthines, are described as agents for treating autoimmune diseases. Also novel methods of manufacture for the derivatives, pharmaceutical compositions thereof, and methods of use therefor are the invention.

18 Claims, No Drawings

OXAZOLO-PYRIMIDINE DERIVATIVES

This is a division of Ser. No. 767,202, filed 8/22/85, now U.S. Pat. No. 4,772,606, which is a continuation-in-part of Ser. No. 660,152, filed 10/12/84, now abandoned.

BACKGROUND OF THE INVENTION

8-Aminoguanine, a compound known since the turn of the century, has been reported to have PNP-activity by R. Parks, et al., in Biochem. Pharm., 31 (2), 163 (1982).

9-(2-Furfuryl)guanine is a known compound described in J. Am. Chem. Soc., 81, 3046 (1959) having no disclosed utility. The present invention is related to novel purine derivatives not obvious to an ordinarily skilled artisan, particularly, 9-heteroaryl guanines as having PNP-inhibiting activity.

8-Amino-9-benzylguanine was discussed at the 16th Annual Graduate Student Meeting in Medicinal Chemistry, University of Michigan, Ann Arbor, Mich. However, the present compounds are not obvious from either the synthesis or biological activity of 8-amino-9-benzylquanine discussed.

With regard to various novel processes of the present invention Ji-Wang Chern, et al, describe "A Convenient Synthesis of 2-N-methoxycarbonylaminooxazolo[5,4-d]pyrimidines" in J. Het. Chem. 21, 1245-6 (1984). A similar synthesis is described by S. Ram, et al, in "A Synthesis of Carbamic Acid[Imidazo-Heteroaromatic] Methyl Ester Derivatives Using Methoxycarbonyl Isothiocynate," Heterocycles, Vol. 22, No. 8, 1984, pp 1789-90, in which methoxycarbonyl isothiocyanate is used in a one pot reagent for the ring closure of an o-diaminopyrimidine derivative to afford a purine derivative possessing the methoxycarbonylamino functionality at position eight. Further, the mechanism of these two synthesis is discussed by Ji-Wang Chern, et al, in "The Novel Ring Opening of an Oxazolo[5,4-d]Pyrimidine and Subsequent Rearrangement to Form an Imidazo[4,5-d]Pyrimidine," Heterocycles, Vol. 22, No. 11, 1984, pp. 2439-2441. None of the disclosures include a disclosure of reactin conditions, or an Ar as a heteroaryl or substituted heteroaaryl, substituent defined hereinafter for the compound of Formula I prepared by the novel processes of the present invention. That is, corresponding Ar groups as defined hereinafter for each of the novel intermediates III, II, and I to be heteroaryl or substituted heteroaryl are not included in the above references and furthermore are not obvious variants thereof.

SUMMARY OF THE INVENTION

The present invention relates to a compound of the formula

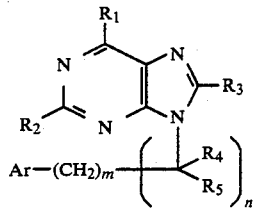

I wherein $R_1$ is OH or SH; $R_2$ is hydrogen, NHR in which R is hydrogen or $COR_6$ where $R_6$ is alkyl of one to four carbon atoms, aryl or arylalxyl; $R_3$ is hydrogen, hydroxyl, mercapto, bromine or NHR where R is hydrogen or $COR_6$ wherein $R_6$ is as defined above; n is zero or one; m is zero, one, two, or three, with the proviso that m or n is at least one; $R_4$ and $R_5$ are each independently hydrogen, alkyl of one to four carbon atoms, hydroxyalxyl of one to four carbon atoms, aryl, arylalkyl or cycloalkyl of three to six carbon atoms, and Ar is heteroaryl or heteroaryl substituted by alkyl, alkoxy of one to four carbon atoms, —C═C—C═C— attached to adjacent carbons so as to form a benzo radical, or halogen; or a pharmaceutically acceptable acid or base addition salt thereof, excluding the compound wherein $R_1$ is OH, $R_2$ is amino, $R_3$ is hydrogen, n is zero, m is one, and $A_r$ is 2-furanyl, i e., 9-(2-furanylmethyl)guanine.

The present invention includes a method of manufacture and a pharmaceutical composition comprising an effective amount of a compound of the Formula I with a pharmaceutically acceptable carrier, as well as a method of treatment of autoimmune diseases such as arthritis, systemic lupus erythematosus, inflammatory bowel diseases, multiple sclerosis, juvenile diabetes, as well as transplantation, viral infections and cancer by administering an effective amount of a compound of the Formula I in unit dosage form to a host of the disease. That is, the amount is the amount effective for treating each of the autoimmune diseases. It is understood, an ordinarily skilled physician would begin with a less than effective amount for treatment and increase the dose until the desired effect is obtained exercising care to administer an amount less than the amount toxic to the host of the disease.

Both the above pharmaceutical composition and method of treatment include as active ingredient 9-(2-furfuryl)guanine.

The present invention also includes the novel intermediates as follows:

(1) A compound of Formula III wherein $R_6$ is alxyl of one to four carbon atoms, aryl, or arylalkyl; n is zero or one; m is zero, one, two, or three, with the proviso that m or n is at least one; $R_4$ and $R_5$ are each independently hydrogen, alkyl of one to four carbon atoms, aryl, arylalxyl, or cycloalkyl of three to six carbon atoms, hydroxyalkyl of one to four carbon atoms, aryl, arylalkyl, or cycloalkyl of three to six carbon atoms, hydroxyalkyl of one to four carbon atoms, and Ar is heteroaryl or heteroaryl substituted by alkyl of one to four carbon atoms, alkoxy of one to four carbon atoms or halogen;

(2) a compound of Formula II wherein $R_6$, n, m, $R_4$, $R_5$, and Ar are as defined above; and (3) a compound of Formula IV wherein n, m, $R_4$, $R_5$, and Ar are as defined above.

Additionally, the novel processes of the present invention are as follows:

(A) A novel process for the preparation of a compound of Formula I, wherein $R_1$ is OH or SH, $R_2$ is NHR wherein R is as defined above, $R_3$ is hydrogen, hydroxyl, mercapto, bromine, or NHR where R is hydrogen or $COR_6$ wherein $R_6$ is as defined above, and n, m, $R_4$, $R_5$, and Ar are also as defined above which comprises heating a compound of the Formula III wherein $R_6$, n, m, $R_4$, $R_5$, and Ar are as defined above to obtain the compound of Formula I wherein $R_1$ is OH and $R_3'$ is $NHCOOR_6$ wherein $R_6$ is as defined above, and if desired, converting said compound to a compound where $R_1$ is S or SH by methods analogous to those known in the art, and if further desired, where $R_3'$ is $NHCOOR_6$ converting the compound to a compound where $R_3$ is hydrogen, or NHR where R is hydrogen or $COR_6$ wherein $R_6$ is as defined above also by known methods.

Particularly, the above process is for the preparation of 8-amino-9-[(2-thienyl)methyl]quanine.

(B) A process for the preparation of a compound of the formula

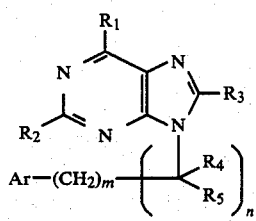

I wherein $R_1$, $R_2$, R, $R_3$, $R_4$, $R_5$, m, n, and Ar are as defined above, with the proviso that $R_3$ is not Br, and $R_3$ is not NHR; which comprises reacting a compound of the formula

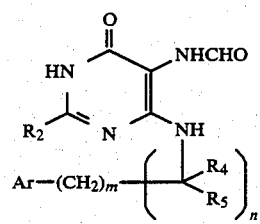

IV with formic acid and formamide at elevated temperatures, to obtain a compound of the formula

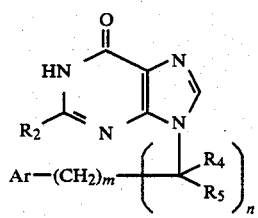

and, if desired, converting by methods analogous to those known in the art the compound into a compound of Formula I wherein $R_1$ is SH and/or $R_3$ is hydroxyl, mercapto, or NHR wherein R is as defined above or a pharmaceutically acceptable acid addition or base salt thereof.

(C) A process for the preparation of a compound of the formula

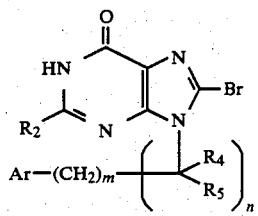

which comprises treating a compound of the formula

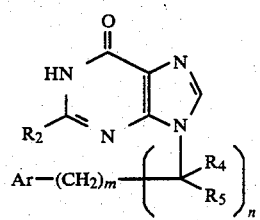

with N-bromosuccinimide in an organic solvent, and, if desired, converting by methods known in the art the resulting compound into a pharmaceutically acceptable acid addition or base salt thereof.

(D) A process for the preparation of a compound of the Formula I wherein $R_3$ is NHR wherein R is as defined above; which comprises reacting a compound of the formula

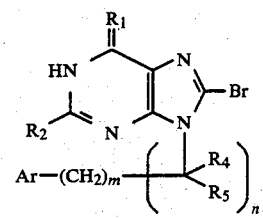

wherein $R_1$, $R_2$, $R_4$, $R_5$, n, m, and Ar is as defined above; with hydrazine at elevated temperatures and, optionally, with Raney nickel in an alcohol solvent, and, if desired, converting the resulting compound where R is hydrogen to a compound where R is $COR_6$ with an alkanoyl halide, aroyl halide, or arylalkanoyl halide in the presence of an organic case, and, if desired, where $R_1$ is O or OH, converting said compound to a compound where $R_1$ is S or SH by known methods, and, if further desired, converting the resulting compound by methods analogous to those known in the art to a pharmaceutically acceptable acid addition or base salt thereof.

(E) A novel process for the preparation of a compound of Formula III wherein $R_6$, n, m, $R_4$, $R_5$, and Ar are as defined above which comprises contacting a compound of the Formula II wherein $R_6$, n, m, $R_4$, $R_5$, and Ar are as defined above, with a coupling agent in the presence of a solvent to obtain the compound of Formula III.

The coupling agent of the process is preferably N,N'-dicyclohexylcarbodiimide. The preferred solvent is anhydrous dimethylformamide.

(F) A novel process for the preparation of a compound of Formula II wherein $R_6$, n, m, $R_4$, $R_5$, and Ar is as defined above which comprises refluxing a compound of Formula IV wherein n, m, $R_4$, $R_5$, and Ar are as defined above in anhydrous methanol with anhydrous HCl then basified and treated with lower alkoxy carbonyl isothiocyanate to obtain the compound of Formula II.

(G) A novel process for the preparation of a compound of Formula IV wherein n, m, $R_4$, $R_5$, and Ar are as defined above which comprises:

step (1) reacting 2-amino-6-chloro-4-pyrimidinol in methoxyethanol with arylalkylamine in the presence of triethylamine;

step (2) then treating the product of step (1) with aqueous sodium nitrite, step (3) reducing the product of step (2) with sodium dithionite in formamide and 90% formic acid to obtain the compound of Formula IV.

Under certain circumstances it is necessary to protect either the N or O of intermediates in the above noted process with suitable protecting groups which are known. Introduction and removal of such suitable oxygen and nitrogen protecting groups are well known in the art of organic chemistry; see for example, (1) "Protective Groups in Organic Chemistry," J. F. W. McOmie, ed., (New York, 1973), pp 43ff, 95ff; (2) J. F. W. McOmie, *Advances in Organic Chemistry*, Vol. 3, 191–281 (1963); (3) R. A. Borssonas, *Advances in Organic Chemistry*, Vol. 3, 159–190 (1963); and (4) J. F. W. McOmie, *Chem. & Ind.*, 603 (1979).

Examples of suitable oxygen protecting groups are benzyl, t-butyldimethylsilyl, methyl, isopropyl, ethyl, tertiary butyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of compounds of Formula I described above are prepared by reacting the appropriate base with a stoichiometric equivalent of the acid compounds of Formula I to obtain pharmacologically acceptable salts thereof.

The compounds of this invention may also exist in hydrated or solvated forms.

The above novel processes beginning with (G) and proceeding through (F), and (E), or to and including (A) to obtain the compound of Formula I wherein $R_1$ is OH and $R_3'$ is $NHCOOR_6$ wherein $R_6$ is as defined above may be conducted in a one pot reaction.

Further, the lower alkoxy carbonylisothiocyanate may itself be added in the novel process (F) above or prepared in situ by suspending potassium thiocyanate in acetonitrile and adding methyl chloroformate to the suspension for a mixture which is heated at reflux in the presence of the basified hydrochloride salt of Formula I in the above process (F).

DETAILED DESCRIPTION

The compounds of Formula I and intermediates of Formula II and IV of the present invention exist in tautomeric forms as purines or guanines as illustrated below. Both forms are included as part of the invention and are indiscriminately described in the specification.

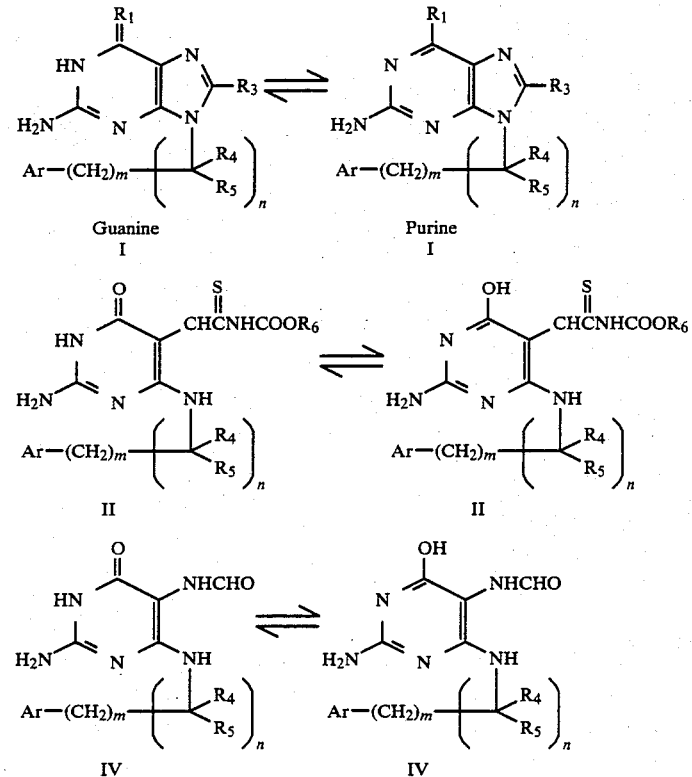

The term "alkyl of one to four carbon atoms" means a straight or branched hydrocarbon chain up to four carbon atoms such as, for example, methyl, ethyl, propyl, isopropyl, butyl, isobutyl, sec-butyl or tertiarybutyl "Hydroxyalkyl of one to four carbon atoms" means the same alkyl radical with a terminal hydroxyl group.

The term "aryl" includes an unsubstituted or substituted aromatic ring such as, phenyl or phenyl substituted by halogen, e.g., fluorine, chlorine, bromine, or iodine, alkyl of one to four carbon atoms, such as methyl or ethyl, hydroxy, alkoxy of one to four carbon atoms, such as methoxy or ethoxy, or trifluoromethyl.

The term "arylalxyl" means an aromatic ring attached to an alxyl chain of up to four carbon atoms, such as unsubstituted or substituted phenylethyl or benzyl where the substituents on the aromatic ring may be the same as defined above.

The term "heteroaryl" means five- or six-membered aromatic ring containing one or more heteroatoms, such as nitrogen, oxygen and sulfur. Preferred radicals are the 2- or 3-furanyl; 2- or 3-thienyl; the 2-, 3- or 4-pyridyl; or 2-, 4-, or 5-thiazolyl radicals.

Pharmaceutically acceptable acid addition salts are those derived from inorganic acids such as hydrochloric, sulfuric and the like, as well as organic acids such as methanesulfonic, toluenesulfonic, tartaric acid, and the like. These salts may also be prepared by standard methods known in the art.

Pharmaceutically acceptable base salts are those derived from inorganic bases such as sodium hydroxide, potassium hydroxide or ammonium hydroxide or organic bases such as arginine, N-methyl glucamine, lysine and the like. These salts may also be prepared by standard methods known in the art.

A preferred embodiment of the present invention is a compound of Formula 1 wherein $R_1$ is OH or SH; $R_2$ is hydrogen or $NH_2$; $R_3$ is hydrogen, bromine or $NH_2$; n is zero or one; m is zero or one, where n or m must be one; $R_4$ and $R_5$ are each independently hydrogen, alkyl of 1–4 carbon atoms or hydroxyalkyl of one to four carbon atoms, and $A_r$ is 2- or 3-furanyl, 2- or 3-thienyl, or 2-, 3- or 4-pyridyl, or 2- or 3-furanyl, 2-, 4-, or 5-thiazolyl, 2- or 3-thienyl, or 2-, 3-, or 4-pyridyl substituted by alkyl of one to four carbon atoms, or a pharmaceutically acceptable acid addition base salt.

Another preferred embodiment of the present invention is a compound of Formula 1 wherein $R_1$ is OH; $R_2$ is $NH_2$; $R_3$ is hydrogen, bromine or $NH_2$; n is 0 or 1; m is 0 or 1, where n or m must be 1, and $A_r$ is 2- or 3-furanyl, 2- or 3-thienyl, 2-, 4-, or 5-thiazolyl, or 2-, 3- or 4-pyridyl, or 2- or 3-furanyl, 2- or 3-thienyl, 2-, 4-, or 5 thiazolyl, or 2-, 3-, or 4-pyridyl substituted by methyl or ethyl, or a pharmaceutically acceptable acid addition or base salt.

Particular embodiments of the present invention include:
9-[(3-pyridyl)methyl]guanine;
9-(2-thenyl)guanine;
9-[(2-pyridyl)methyl]guanine;
9-[(5-ethyl-2-thienyl)methyl]guanine;
8-bromo-9-(2-thienylmethyl)guanine;
8-bromo-9-(5-ethyl-2-thenyl)guanine;
8-bromo-9-(2-furfuryl)guanine;
8-bromo-9-[(3-pyridyl)methyl]guanine;
8-amino-9-(5-ethyl-2-thenyl)guanine;
8-amino-9-(2-thienylmethyl)guanine, and
8-amino-[9-3-pyridyl)methyl]guanine.

The most preferred compound is 8-amino-9-(2-thienylmethyl)guanine.

The 8-bromo compounds are not only useful pharmacologically but are also useful as intermediates for preparing certain compounds of the present invention.

The compounds of Formula I may be prepared according to Methods B, A, and/or C as shown in the following Schemes 1, 2, and 3, respectively. Generally, Method A is preferred.

I. Scheme 1 - Method B

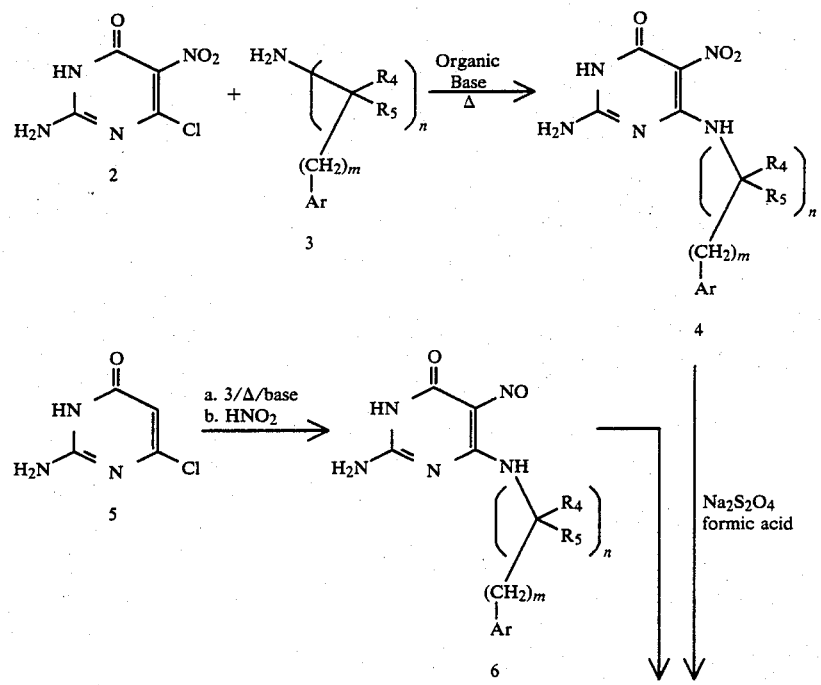

-continued
I. Scheme 1 - Method B

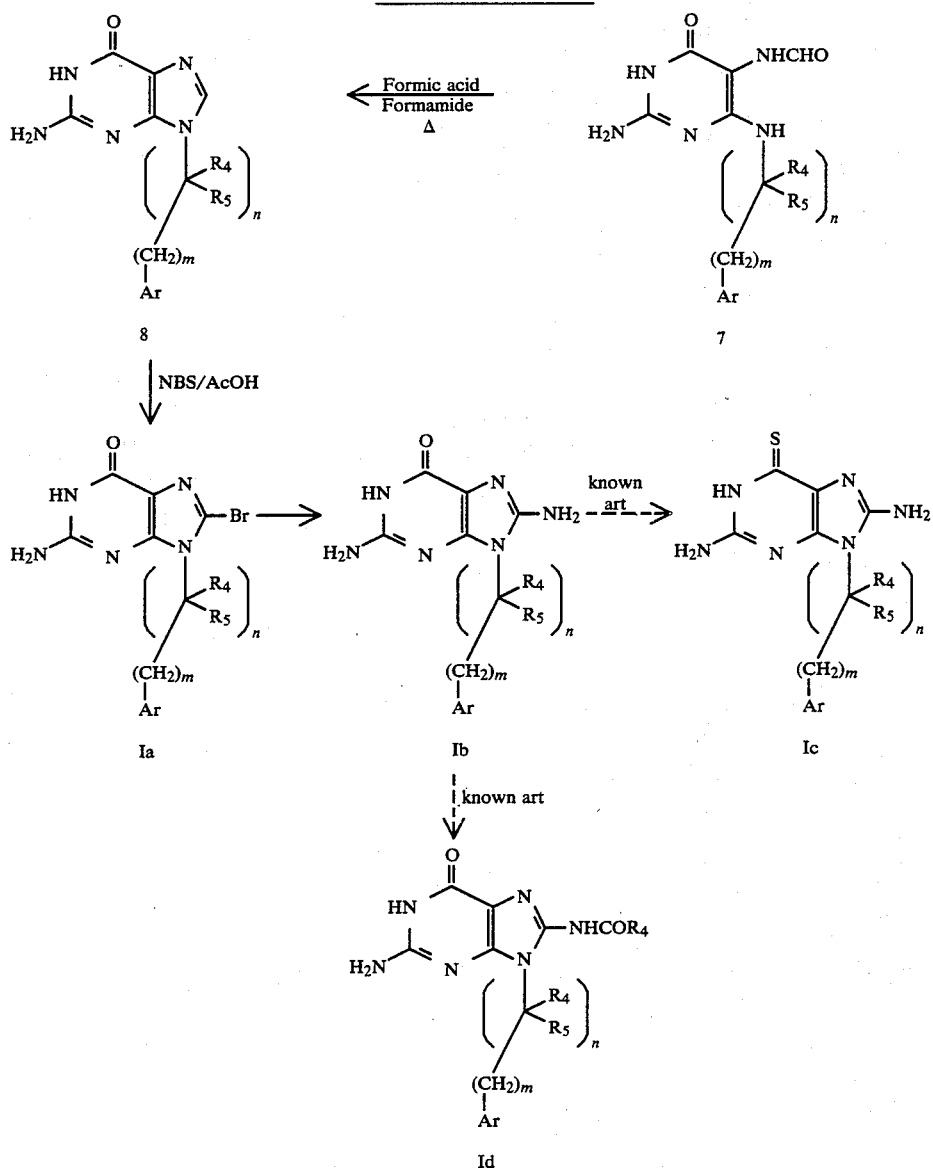

II. Method B-Discussion

Compounds of Formula 8 above may also be used as starting materials and may be prepared by reacting 2-amino-6-chloro-4-hydroxy-5-nitropyrimidine, the compound of formula 2 described in J. Chem. Soc., 1962, p. 4186, with the appropriate heteroaryl (alxyl) amine of formula 3 in the presence of an organic case at elevated temperatures. The resulting compound of the formula 4 is then treated with sodium dithionite and formic acid followed by further treatment with formic acid and formamide at elevated temperatures to afford the compound of Formula 8.

Alternative, starting materials of Formula 8 may be prepared according to a modified method of C. W. Noelland, R. K. Robins in J. Med. Chem., 5, 558, (1962) starting with a compound of the Formula -5 which is reacted with an appropriate heteroaryl alkyl amine of Formula 3, then with nitrous acid to form the 5-nitrosopyrimidine, 6, which is reduced and ring closed by treatment with sodium dithionite, formic acid and formamide as described above.

The heteroaryl (alkyl) amines of Formula 3 are either commercially available or may be prepared by known methods.

Treatment of a compound of Formula 8 with N-bromosuccinimide in acetic acid, dimethylformamide or methanol produces a compound of Formula 1a which when treated with hydrazine hydrate gives the hydrazine or directly the 8-amino derivative of Formula 1b. The reaction of the 8-bromo compound with hydrazine may or may not proceed entirely to the 8-amino compound. Thus when the 8-hydrazine compound is obtained, it may be further reacted with Raney nickel to allow the reduction to go to completion and afford the desired 8-amino compound. Compounds of formula 1b may be further converted by known methods to provide $R_6$ substituents of formula 1d or, where $R_1$ is O, converting said compound to a compound of formula 1c where $R_1$ is S by reacting the said compound with P$_2$S$_5$ in presence of a base such as pyridine (examples given).
III. Scheme 2 - Method A
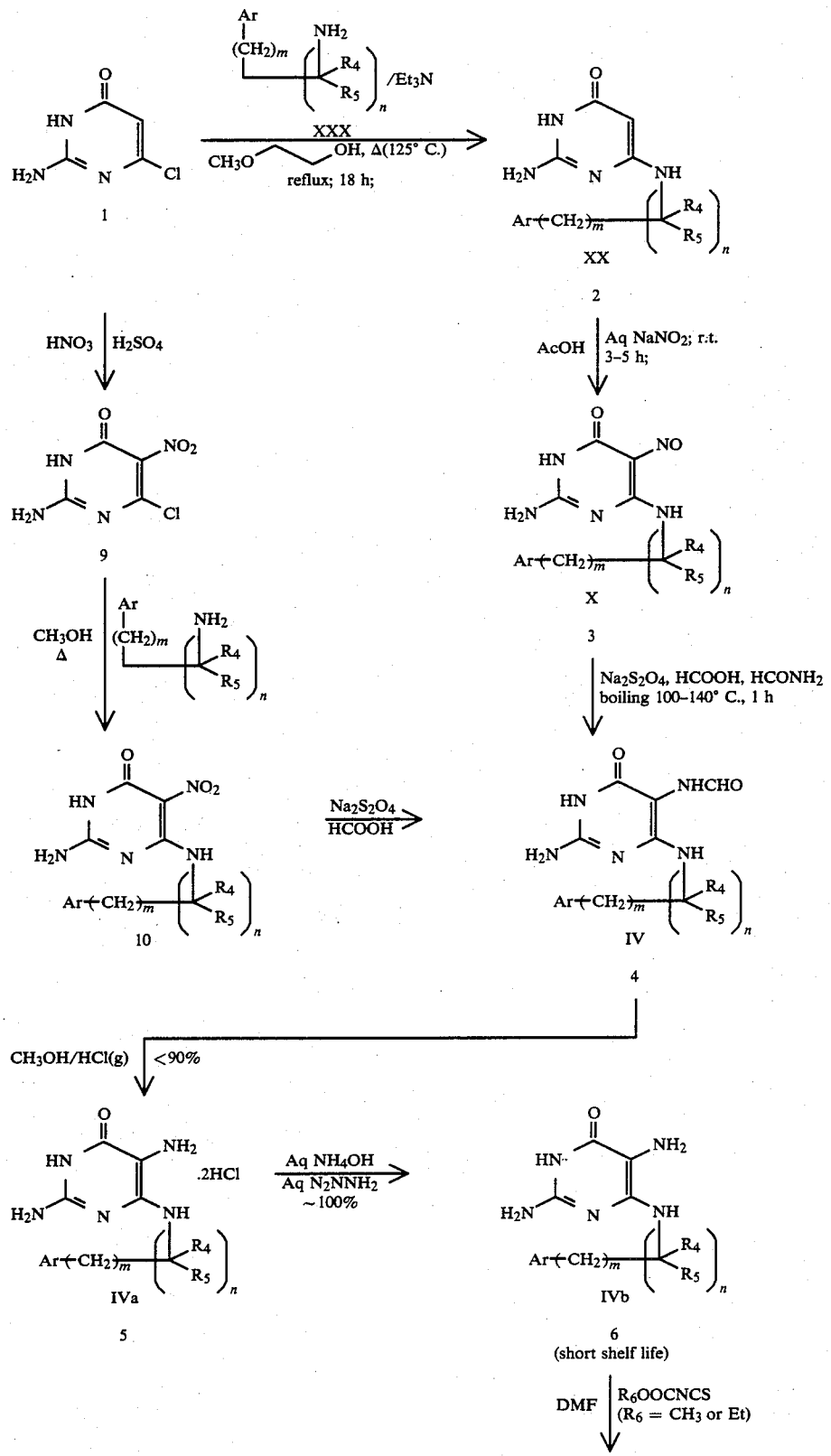

III. Scheme 2 - Method A

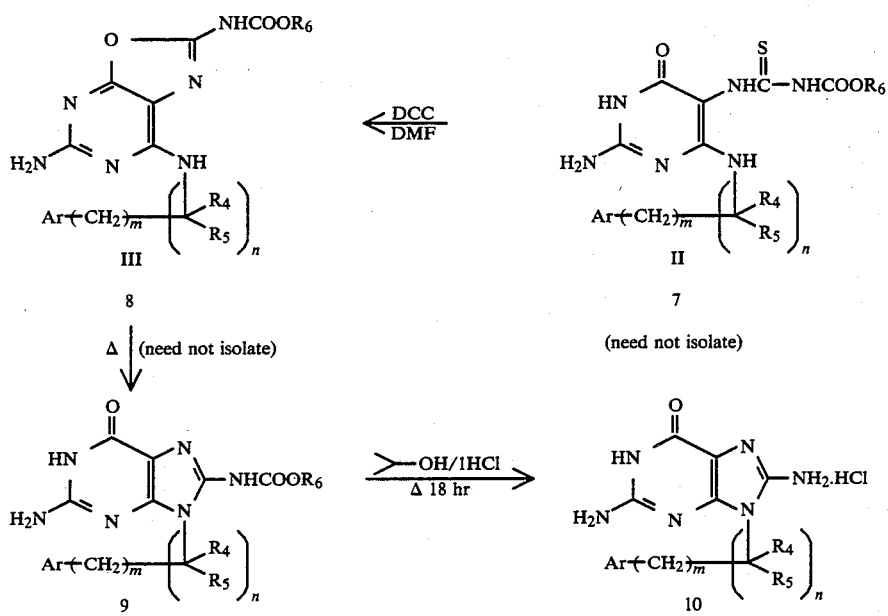

IV. Scheme 3 - Method C

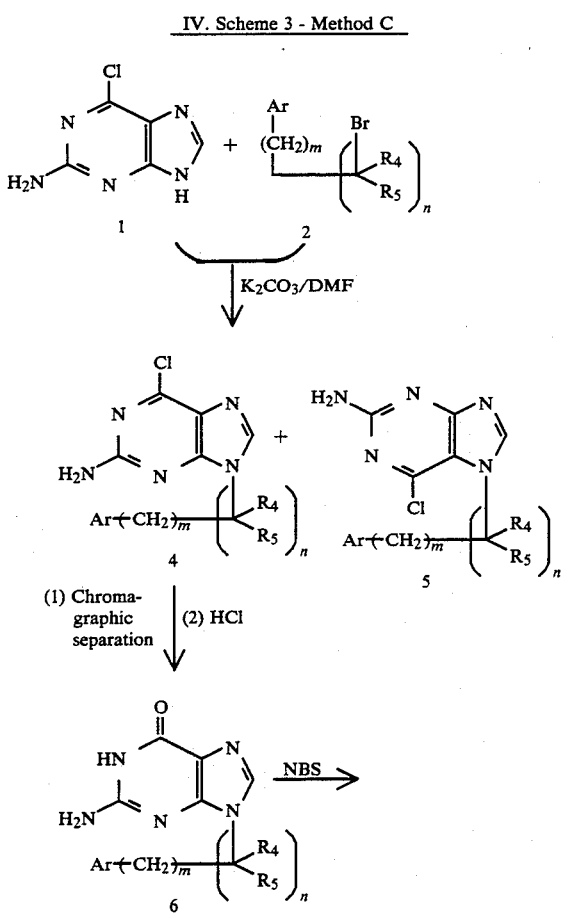

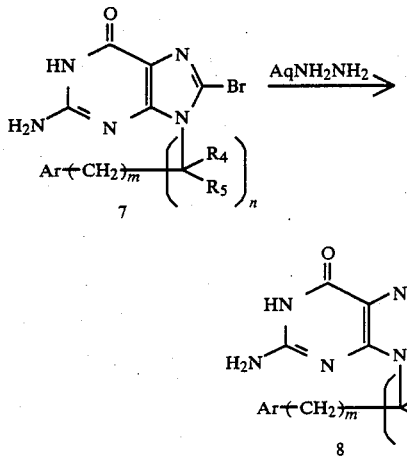

Generally, the processes of the present invention as shown in Scheme 2 above are as follows.

A 2-amino-6-chloro-4-pyrimidinol, that may be in the monohydrate form, is suspended in methoxyethanol, in the presence of excess amine or an organic base such as triethylamine. The compound of Formula XXX having n, m, $R_4$, $R_5$, and Ar as defined above is added to the suspension and heated optically to a temperature at which the suspension refluxes. Refluxing is continued until thin layer chromatography, for example, with 20% methanol in methylene chloride, shows the reaction producing a compound of Formula XX wherein n, m, $R_4$, $R_5$, and Ar are as defined above is complete.

The reaction mixture having the compound of Formula XX is then diluted with water and treated with sodium nitrite in the presence of acetic acid. A nitroso of the Formula X again having n, m, $R_4$, $R_5$, and Ar as defined above is obtained from the treatment by the nitrite as evidenced by a color change and precipitate.

The temperature of the treatment is at about room temperature.

The treatment mixture having therein the nitroso of Formula X is contacted with sodium dithionite in a solvent mixture such as formamide, formic acid, at a temperature of from 60°–90° C., preferably from 70°–80° C. The temperature is then raised to the boiling point of the solvent mixture, approximately 130°–140° C. for up to an hour, preferably at least 20 minutes, or when the color of the nitroso containing mixture described above disappears and an inorganic salt precipitates. The product of this contact is a compound of the Formula IV wherein n, m, $R_4$, $R_5$, and Ar are as defined above.

Subsequently, the compound of Formula IV is dried and suspended in an anhydrous solvent such as methanol, ethanol, and the like. The suspension is then treated with a dry acid such as HCl, to form the acid salt shown as Formula IVa, wherein n, m, $R_4$, $R_5$, and Ar are as defined above, or salt corresponding to the acid used for the treatment.

The salt IVa is basified with a concentrated mixture of $NH_4OH$ and 97% hydrazine to obtain a base of the Formula IVb wherein n, m, $R_4$, $R_5$, and Ar are as defined above. The base is unstable, however, is dried, for example in a vacuum over $P_2O_5$.

The dried free base IVb is added to a solution of $R_6OOCNCS$ wherein $R_6$ is as defined above. The solution of $R_6OOCNCS$ may be prepared by suspending potassium thiocyanate in a solvent such as acetonitrile and treating with slightly less than an equivalent of $ClCOOR_6$ wherein $R_6$ is as defined above at reflux for about one hour, cooled, then stirred to insure all of the alkylchloroformate is reacted before the base IVb is added. The reaction of dried free base IVb with the $R_6OOCNCS$ is monitored to completion with thin-layer chromatography using silica in 20% methanol in methylene chloride to obtain a compound of Formula II wherein $R_6$, n, m, $R_4$, $R_5$, and Ar is as defined above.

A mixture of the compound of Formula II and a coupling agent such as N,N'-dicyclohexylcarbodiimide, in a solvent such as anhydrous dimethylformamide, is stirred at about room temperature until completion of the reaction is shown by thin layer chromatograph to yield a compound of Formula III wherein $R_6$, n, m, $R_4$, $R_5$, and Ar are as defined above.

The reaction mixture having the compound of Formula III and anhydrous potassium carbonate are suspended in a solvent such as anhydrous methanol, and refluxed until thin layer chromatography shows the reaction producing a compound of Formula I wherein $R_1$ is O or OH, $R_3'$ is $NHCOOR_6$, wherein $R_6$ is as defined above and n, m, $R_4$, $R_5$, and Ar are as defined above.

The compound of Formula I wherein $R_1$, is O and OH and $R_3'$ is $NHCOOR_6$ may then, if desired be used to produce by known methods a compound of Formula I wherein $R_3$ is NHR wherein R is as defined above other than $COOR_6$.

Likewise, a compound of Formula I wherein $R_1$ is S or SH may be prepared by known methods from the compounds of Formula I wherein $R_1$ is O or OH.

The preparation of compounds IV, II, III, and I may be carried out in one pot. However, separation and purification of each of the compounds IV, II, III, or I may be effected by conventional methods, if desired.

Generally the processes of the present invention as shown in Scheme 3 - Method C above are as follows:

A mixture of 2-amino-6-chloropurine, potassium carbonate, and the starting material of the formula shown as 2 in Scheme 3 - Method C, that is generally commercially available or can be prepared by methods analogous to those known in the art, are stirred under nitrogen for from about 2 to 48 hours. A mixture of 7- and 9-substituted chloropurines shown as Formula 4 and Formula 5 in Scheme 3 - Method C are obtained. The desired compound of Formula 4 is separated and treated with an aqueous acid such as HCl followed by addition of a weak solution of a base such as NaOH. The mixture is heated to assure it is neutralized followed by conventional separation of the desired product of Formula I wherein $R_3$ is hydrogen. Subsequently, reactions to produce compounds of Formula 7 and Formula 8 as shown in Scheme 3 - Method C are described above for corresponding steps in Scheme I - Method B.

The compounds of the present invention have been shown to exhibit significant enzyme inhibition activity and cytotoxic activity. In the purine nucleoside phosphorylase (PNP-4) enzyme assay, total inhibition was achieved at a concentration less than about 300 micromoles on certain compounds of the present invention. PNP-4 activity was measured radiochemically by measuring the formation of $[^{14}\text{-C}]$-hypoxanthine from $[^{14}\text{-C}]$inosine [Biomedicine, 33, 39 (1980)] using human erythrocyte as the enzyme source. The same compounds also were found by a standard test (HTBA-1) [Science, 214, 1137, (1981)] to be selectively cytotoxic for T-cells in the presence of 2'-deoxyguanosine at a similar concentration range and nontoxic to B-cell in the presence of the same amount of 2'-deoxyguanosine. Representative examples are shown in the activity table.

| Example Number | $Ar^1$ | Method of Preparation | PNP-4 $IC_{50}$ ($\mu M$) | HTBA-1 T-Cell +dGuo (10 $\mu M$) $IC_{50}$ ($\mu M$) |
|---|---|---|---|---|
| 1 | 3-Py | B | 21.9 | 54.1 |
| 2 or 9a | 2-Th | A or B | 0.17 | 0.83 |
| 3 | 2-Th-5-Et | B | 0.93 | 4.15 |
| 9b | 2-Fu | B or A | 0.25 | 2.57 |
| 9c | 3-Th | A, B, or C | 0.085 | 0.49 |
| 9d | 2-Th-3-$CH_3$ | B | 4.05 | 8.6 |
| 16Ad | 3-TH-2-$CH_3$ | A | 1.72 | 18.2 |
| 16Ac | $CH_2$-2-Th | A | 6.25 | 17.6 |
| 16Ak | 3-TH-5-$CH_3$ | A | 0.63 | 2.8 |

Activity Table -continued

| Example Number | Ar¹ | Method of Preparation | PNP-4 IC$_{50}$ (μM) | HTBA-1 T-Cell +dGuo (10 μM) IC$_{50}$ (μM) |
| --- | --- | --- | --- | --- |
| 16Ag | benzo[b]thien-2-yl | A | 8.45 | >12.5 |
| 9e | benzo[b]thien-3-yl | B | 140 | |
| 16Ae | 2-Th-5-Me | A | | |
| 16Af | 2-Py | A | 4.6 | |

¹Py = pyridine, Th = thiophene, Fu = furan

Since T-cells play a central role in immune response, use of the compounds of the invention is contemplated for the immunoregulation of autoimmune disease such as rheumatoid arthritis, systemic lupus erythematosus, inflammatory bowel disease, multiple sclerosis, myasthemia gravis, transplantation, juvenile diabetes, cancer, and viral diseases. The present invention thus includes compositions containing a compound of Formula I in treating disease such as autoimmune disease characterized by abnormal immune response in warmblooded animals. According to this aspect of the invention, the properties of the compounds of the invention are utilized by administering to a warmblooded animal an effective amount of a pharmaceutical composition containing as the active ingredient at least about 0.1 percent by weight, based on the total weight of the composition of at least one such compound of the invention.

Pharmaceutical compositions of the invention can be formulated in any suitable way, preferably with an inert carrier for administration orally, parenterally, ophthalmically, topically, or by suppository.

For example, the compounds of the present invention are formulated into dosage forms such as tablets or syrups by blending with an inert pharmaceutical carrier such as lactose or simple syrup by methods well known in the art. For injectable dosage forms, they are formulated with vehicles such as water, propylene glycol, peanut oil, sesame oil, and the like. In these dosage forms, the active ingredient is from about 0.05 grams to 0.5 grams per dosage unit.

The present invention is further illustrated by way of the following examples.

EXAMPLE 1

9-[(3-Pyridinyl)methyl]guanine

3-Pyridylmethylamine (15.8 ml; 0.1517 mole) was added to a suspension of 2-amino-6-chloro-4-hydroxy-5-nitropyrimidine (14.45 g; 0.0758 mol) in isopropanol (600 ml). The mixture was heated under reflux for two hours and then stirred overnight at room temperature when the product, 2-amino-4-hydroxy-6-[(3-pyridyl)-methylamino]-5-nitropyrimidine, crystallized out. The product was filtered, washed with water, and air dried.

The crude nitropyrimidine (25.32 g) from above was suspended in formamide (150 ml) and 90% formic acid (50 ml) and the suspension was warmed to 70° C. in a water bath. Sodium dithionite was carefully added to the warm suspension and then boiled for 15–20 minutes. The reaction mixture was diluted with hot water (300 ml), treated with charcoal and then boiled for an additional 20–25 minutes, filtered through celite, cooled and concentrated under reduced pressure to give formamido-pyrimidine which was collected by filtration, washed with acetone, and dried under vacuum at 56° C.

The above product was resuspended in formamide (100 ml) and formic acid (8 ml) and was heated under reflux for 3.5 hours, poured onto 400 ml ice-water and then filtered. Two crystallization from boiling water gave the analytical sample of the desired product (4.5 g) mp >300° C.

EXAMPLE 2

The procedure described in Example 1 was repeated to prepare the following 9-(heteroaryl or substituted heteroaryl)methyl guanines, starting from appropriate heteroaryl or substituted heteroaryl methylamines. 9-(2-Thienylmethyl)guanine, mp >300° C. 9-[(2-Pyridinyl)-methyl]guanine, mp >300° C. 9-(2-Furanylmethyl)guanine, mp 296°–299° C., dec. (Known Compound: J. Am. Chem. Soc., 1959, 81:3046.) 9-[(3-methyl-2-thienyl)methyl]guanine, mp >290° C. (dec). 9-[(2-methyl-3-thienyl)methyl]guanine, mp >270° C. (dec). 9-[(benzo[b]thien-3-yl)methyl]guanine, mp >300° C. (dec). 9-(3-thienylmethyl)guanine, mp 320°–322° C. (dec).

EXAMPLE 2A

2-Amino-9-[(2-thienyl)methyl]-6-chloropurine

A mixture of 2-amino-6-chloropurine (Aldrich Chemical Co.) (7.47 g; 0.44 mol), potassium carbonate (6.64 g; 0.048 mol), and 3-thenylbromide (see U.S. Pat. No. 3,746,724) (7.8 g; 0.044 mol) in DMF (200 ml) was stirred under nitrogen at room temperature for 48 hours. The mixture was filtered and the filtrate evaporated to dryness under vacuum, ethyl ether was added and the precipitate was collected by filtration to give a mixture of 7- and 9-substituted chloropurines. A sample of pure 9isomer was prepared by chromatography on silica gel with 5% methanol/methylene chloride as the eluting solvent to separate it from the 7-isomer. Analytical sample was obtained by crystallization from acetonemethanol mixture, yield 2.36 g, mp softens at 185° C. (dec) and then melts at 203°–204° C. (dec).

EXAMPLE 2B

The procedure described in Example 2A was repeated to prepare the following 2-amino-9-[(heteroaryl or substituted heteroaryl)methyl]-6-chloropurines, starting from appropriate heteroaryl or substituted heteroaryl methylhalides.

2-Amino-9-[(2,5-dimethyl-3-thienyl)methyl]-6-chloropurine, mp 190°-192° C. (starting material 2,5-dimethyl-3-thenyl chloride was prepared according to the lit. procedure; Buu-Hoi and Nguyen-Hoan, Rec. Trav. Chim, 1949, 68:5).

2-Amino-9-(3-furanylmethyl)-6-chloropurine (starting material 3-furfurylchloride was prepared according to lit. procedure; S. P. Tanis, Tet. Letts., 1982, 23:3115).

EXAMPLE 2C

9-[(2,5-dimethyl-3-thienyl)methyl]guanine

A mixture of 2-amino-9-[(2,5-dimethyl-3-thienyl)methyl]-6-chloropurine (3.8 g, 0.0129 mol) and 2N HCl was heated on a steambath for 3.0 hours and then heated under reflux for another hour. At the end of this time 1N NaOH solution was added to the solution till basic and the mixture was heated for another five minutes. The mixture was then acidified with acetic acid, cooled, and filtered to give 3.6 g, of the product. An analytical sample was obtained by chromatography over silica gel using 10% methanol/chloroform as eluting solvent, mp >300° C. (dec).

EXAMPLE 2D

The procedure described in Example 2C was repeated to prepared 9-(3-thenyl)guanine, mp 320°-322° C. (dec).

EXAMPLE 2E

9-(3-furanylmethyl)guanine

The crude 2-amino-9-(3-furfuryl)-6-chloropurine (4.74 g, 0.019 mol) was suspended in methanol (175 ml) and a solution of sodium methoxide, prepared from sodium metal (1.75 g; 0.076 g atom), and methanol (75 ml), was slowly added to the suspension, followed by 2-mercaptoethanol (6.1 ml=6.8 g; 0.087 mol) and water (0.35 ml). The reaction mixture was heated under reflux ($N_2$ atm) for two hours, when an additional amount of sodium methoxide from 1.14 g sodium (0.05 g atom) and 25 ml methanol was added. After an additional 2.5 hours reflux, the reaction mixture was concentrated under vacuum to 75 ml and then diluted with water (200 ml), and acidified with acetic acid (pH 5.5). The white ppt. was filtered, washed with water, and dried, yield 4.05 g; mp 308°-310° C.

EXAMPLE 3

9-[(5-Ethyl-2-thienyl)methyl]guanine

2-Amino-6-chloro-4-pyrimidinol, monohydrate (22.96 g; 0.1193 mole) was suspended in methoxyethanol (300 ml) and 5-ethyl-2-thenylamine (16.58 g; 0.1193 mole) prepared from 2-ethyltniopnene according to the Lit. Procedure, (JACS, 1948, 70:4018) was added to the suspension. The resulting solution was heated under reflux for one hour and then 16.8 ml of triethylamine was added and the refluxing continued for an additional 18 hours. The reaction mixture was poured into ice water (600 ml), diluted with acetic acid (100 ml) and then treated with a solution of sodium nitrite (16 g) in water (100 ml). The mixture was stirred at room temperature for 1.5 hours and the resulting salmon colored nitroso compound was collected by filtration and washed with water.

The crude nitrosopyrimidine was then reduced with sodium dithionite in formamide (200 ml) and 90% formic acid (100 ml) at 70° C. and then boiled for 20 minutes The reaction mixture was diluted with water (300 ml) and the boiling continued for an additional 30 minutes, filtered hot, and then allowed to crystallize in the refrigerator. The crude N-formyl derivative (28 g) was collected by filtration, washed with water and air dried and then cyclized with formic acid (10 ml) and formamide (100 ml) at reflux temperature for four hours. The hot reaction mixture was poured into 500 ml of ice water to give the crude guanine which was then purified by dissolving in boiling 1.5N HCl, treating with charcoal and then precipitating with ammonium hydroxide. The crude guanine was then redissolved in hot 1N NaOH solution, treated with charcoal, filtered and the filtrate acidified with acetic acid to give the desired product which was used in the next step without further purification.

EXAMPLE 4

The procedure described in Example 3 was repeated to prepare 9-(2-thenyl)guanine, mp >300° C. starting from 2-amino-6-chloro-4-pyrimidinol and 2-thenylamine.

EXAMPLE 5

8-Bromo-9-(2-thienylmethyl)guanine

N-Bromosuccinimide (2.82 g; 15.7 mmol) was added to a cold (0° C.) suspension of 9-(2-thenyl) guanine (3.5 g; 14.1 mmol) in DMF (100 ml) and the mixture was stirred for 30 minutes at 0° C. and then at room temperature for 24 hours. The reaction mixture was then diluted with 75 ml of water and filtered. Recrystallization of the product from DMF gave the analytical sample, yield 3.1 g; mp 294°-295° C. (dec).

EXAMPLE 6

The procedure described in Example 5 was repeated to prepare the following 8-bromo-9-[(substituted heteroaryl)methyl]guanines, starting from appropriate 9-[(substituted heteroaryl)methyl]guanines in each case.

8-bromo-9-(5-ethyl-2-thienylmethyl)guanine
8-bromo-9-(2-furanylmethyl)guanine, mp >340° C.
8-bromo-9-[(2-methyl-3-thienyl)methyl]guanine, mp >280° C. (dec).
8-bromo-9-[(benzo[b]thien-3-yl)methyl]guanine, mp 258°-260° C. (dec).

EXAMPLE 7

8-Bromo-9-[(3-pyridinyl)methyl]guanine

N-Bromosuccinimide (1.59 g; 8.95 mmol) was added to a suspension of 9-[(3-pyridyl)methyl]guanine (2.0 g; 8.14 mmol) in glacial acetic acid (20 ml) and the mixture was stirred at room temperature for 3.5 hours. The reaction mixture was concentrated under reduced pressure and then diluted with water and filtered. The crude product was triturated with water, filtered, and washed with water and dried. Yield 1.91 g; mp >300° C.

EXAMPLE 8

8-Amino-9-(5-ethyl-2-thienylmethyl)guanine

A mixture of 8-bromo-9-(5-ethyl-2-thenyl)guanine (6.5 g; 18.3 mmol) and 60% aqueous hydrazine (200 ml) was heated to reflux under nitrogen atmosphere for 20 hours. 2-Methoxyethanol (50 ml) was added and the refluxing continued for an additional 48 hours in the open air. The orange-brown solution was cooled, diluted with water (150 ml) and allowed to crystallize in the refrigerator overnight. The crude product thus obtained was converted to the hydrochloride salt by recrystallizing from boiling isopropanol and 1N HCl. Yield, 0.49 g; mp 215°–218° C., dec.

EXAMPLE 9

The procedure described in Example 8 was repeated to prepare the following 8-amino-9-[(substituted heteroaryl)methyl)guanines, starting from appropriate 8-bromo-9-[(substituted heteroaryl)methyl]guanines: 8-Amino-9-[(3-pyridyl)methyl]guanine, mp >300° C. and additionally, the following compounds a through e were prepared.
a. 8-Amino-9-(2-thenyl)guanine or 8-amino-9-[(2-thienyl)methyl]guanine as hydrochloride salt, 0.5 H$_2$O, mp 223°–226° C. (dec).
b. 8-Amino-9-(2-furanylmethyl)guanine monohydrochloride, 1.0 H$_2$O, mp 197°–199° C. (dec).
c. 8-Amino-9-[(3-thienyl)methyl]guanine, monohydrochloride, monohydrate, mp 275°–278° C. (dec).
d. 8-Amino-9-[(3-methyl-2-thienyl)methyl]guanine, 0.25 H$_2$O, mp 290° C. (dec).
e. 8-Amino-9-[(benzo[b]thien-3-yl)methyl]guanine, 0.5 H$_2$O, mp >300° C. (dec).

Starting materials, such as 2-, 3-, or 4-pyridylmethylamines, 2-thenylamine also called 2-(aminomethyl)thiophene or 2-thiophene methylamine, and 2-furfurylamine are commercially available (for example, Aldrich Chemical Company). The substituted thenylamines were synthesized from the substituted thiophenes using a general literature procedure. (H. D. Hartough and S. L. Meisel, J. Am. Chem. Soc., 1948, 70:4018).

2-Amino-6-chloro-4-hydroxy-5-nitropyrimidine was synthesized according to a method described in the literature (A. Stuart and H. C. S. Wood, J. Chem. Soc., 1963:4186).

2-Amino-6-chloro-4-pyrimidinol monohydrate was purchased from Aldrich Chemical Company.

EXAMPLE 10

2-Amino-4[[(2-thienyl)methyl]amino]-5-(formamido)-6-pyrimidinol (a compound of Scheme 2 Formula IV wherein n is one, m is zero, R$_4$ and R$_5$ are hydrogen, Ar is 2-thienyl)

2-Amino-6-chloro-4-pyrimidinol, monohydrate (85%, 100.0 g, 0.5197 mole) was suspended in methoxyethanol (700 ml) and 2-thiophenemethylamine (96%, 61.3 g, 0.5197 mole) is added to the suspension. The mixture was heated under reflux for two hours and then 73 ml (d=0.726, 0.52 mole) of triethylamine was added and the refluxing continued for an additional 18 hours. (The reaction was followed by TLC: 20% methanol-CHCl$_3$.) The reaction mixture was poured into ice water (1000 ml), diluted with acetic acid (400 ml), and then treated with a solution of sodium nitrite (80 g, 1.16 mole) in water (300 ml). The mixture was stirred at room temperature for four hours, and the resulting reddish colored nitroso compound (X) was collected by filtration and washed with water (the reaction was followed by observing the color change in the formation of the precipitate).

The crude nitrosopyrimidine of Formula X, (of Scheme 2, Formula X, wherein n is one, m is zero, R$_4$ and R$_5$ are each hydrogen and Ar is 2-thienyl) prepared above was divided into two batches and each in turn was then reduced with sodium dithionite (>90% 70 g, 0.36 mole) in formamide (300 ml) and 90% formic acid (300 ml) at 80° C. and then boiled for 20 minutes. The temperature was approximately 130°–140° C. at this point. The reaction was complete when the red color completely disappears and inorganic salt precipitates. The reaction mixture was diluted with water (300 ml) and the boiling continued for an additional 30 minutes, filtered hot, and then allowed to crystallize in the refrigerator. The reaction was monitored to completion by TLC (SiO$_2$; 20% CH$_3$OH in CHCl$_3$. The crude N-formyl derivative, 2-amino-4[[(2-thienyl)methyl]amino]-5-(formamido)-6-pyrimidinol, (100 g) was collected by filtration, washed with water, and dried and used in the next step without further purification in most cases.

EXAMPLE 10A

The procedure described in Example 10 was repeated to prepare 2-Amino-[[(3-thienyl)methyl]amino]-5-(formamido)-6-pyrimidinol starting from 3-thiophene methylamine and 2-amino-6-chloro-4-pyrimidinol.

EXAMPLE 11

2-Amino-4-[[(2-furanylmethyl)amino]-5-(formamido)-6-pyrimidinol

A mixture of 2-amino-6-chloro-5-nitro-4-pyrimidinol (J. CHem. Soc., 1962, p 4186) (31.5 g; 0.15 mol) methanol (1200 ml) and furfurylamine (29.1 g; 0.3 mol) was stirred and heated under reflux (N$_2$ atm) for six hours. The reaction mixture was cooled, filtered, washed with water, and air dried to give 34.43 g of yellow solid, mp 286°–289° C. (dec), which was used in the next reaction.

The crude nitropyrimidine (33.9 g; 0.135 mol) was suspended in formamide (290 ml) and 88% formic acid (145 ml), and then warmed up to 80° C. Sodium dithionite (57 g; 0.327 mol) was slowly added to the warm (80°–85° C.) suspension over a period of 50 minutes, maintained at the temperature (–85° C.) for another 30 minutes, then diluted with boiling water (1200 ml), and heated the mixture around 85° C. for another 20 minutes when tan colored crystals were formed. The product was filtered off, washed with water, and dried over P$_2$O$_5$ under vacuum overnight. Yield, 23.4 g, mp 246°–247° C. (dec). In most cases these compounds were carried through the reaction sequences without characterization.

EXAMPLE 11A

The procedure described in Example 11 was repeated to prepare the following 2-amino-4[(heteroaryl or substituted heteroaryl)methyl]amino]-5-(formamido)-6-pyrimidinols, (Table 1) starting from appropriate heteroaryl or substituted heteroaryl methylamines and 2-amino-6-chloro-5-nitro-4-pyrimidinol.

TABLE 1

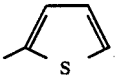

| Ar | or | Ar |
|---|---|---|
| 2-Thienyl | | 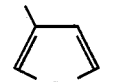 |
| 3-Thienyl | | 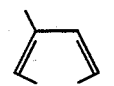 |
| 3-Furanyl | | 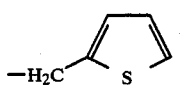 |
| (2-thienyl)methyl | | 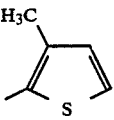 |
| 3-Me-2-thienyl | | 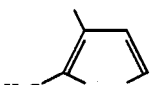 |
| 2-Me-3-thienyl | | 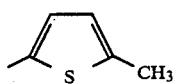 |
| 5-Me-2-thienyl | | 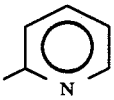 |
| 2-Pyridinyl | | 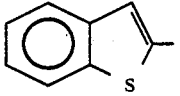 |
| Benzo[b]thien-2-yl | | 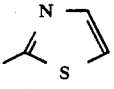 |
| 2-thiazolyl | | 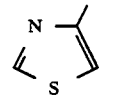 |
| 4-thiazolyl | | 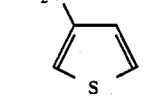 |
| (3-thienyl)methyl | | 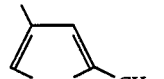 |

TABLE 1-continued

| Ar | or | Ar |
|---|---|---|
| 5-Me-3-thienyl | | 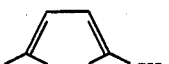 |
| 5-Me-2-furanyl | | 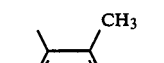 |
| 4-Me-3-thienyl | | 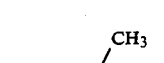 |
| 4-Me-2-thienyl | | |

EXAMPLE 12

2,5-Diamino-4-[(2-thienylmethyl)amino]pyrimidin-6-ol, dihydrochloride (a compound of Scheme 2, Formula IVa, wherein n is one, m is zero, $R_4$ and $R_5$ are each hydrogen, and Ar is 2-thienyl)

The crude N-formyl derivative as prepared in Example 10 above (40 g, 0.1508 mole) was suspended in anhydrous methanol (500 ml) and a stream of dry HCl (g) was passed through the solution while heating the mixture at reflux. The reaction was continued for 2.5 hour when a clear solution was formed followed by a crystalline precipitate. The mixture was cooled in an ice bath and then filtered to give the salt, 2,5-diamino-4-[(2-thienylmethyl)amino]pyrimidine-6-ol, dihydrochloride, (28.6 g). Concentration of the mother liquor gave an additional amount of the salt (8.65 g). Total yield, 37.25 g (79%). The material was carried on without further purification.

Alternatively, the N-formyl derivative was refluxed with 5% methanolic-HCl (g) to give the desired diamine. 2 HCl salt.

EXAMPLE 12A

The procedure described in Example 12 was repeated to prepare the following 2,5-diamino-4-[[(heteroaryl or substituted heteroaryl)methyl]amino]pyrimidin-6-ol, as dihydrochloride salt (Table 2), starting from appropriate 2-amino-4-[[(heteroaryl or substituted heteroaryl)methyl]amino]-5-(formamido)-6-pyrimidinol (Table 1).

TABLE 2

| Ar | or | Ar |
|---|---|---|
| 3-Thienyl | | 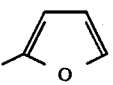 |
| 2-Furanyl | |  |
| 3-Furanyl | | 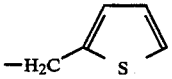 |
| (2-thienyl)methyl | | 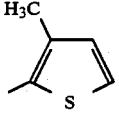 |
| 3-Me-2-thienyl | | 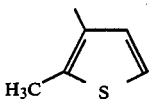 |
| 2-Me-3-thienyl | | 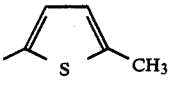 |
| 5-Me-2-thienyl | | 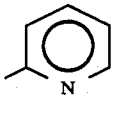 |
| 2-Pyridinyl | | 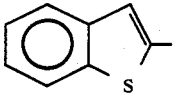 |
| Benzo[b]thien-2-yl | | 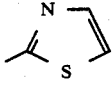 |
| 2-thiazolyl | | 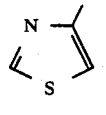 |
| 4-thiazolyl | | 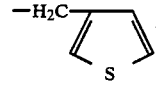 |
| (3-thienyl)methyl | | 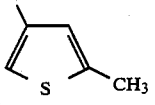 |

TABLE 2-continued

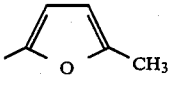

| Ar | or | Ar |
|---|---|---|
| 5-Me-3-thienyl | | 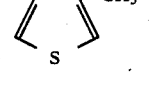 |
| 5-Me-2-furanyl | | 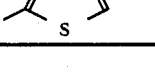 |
| 4-Me-3-thienyl | | |
| 4-Me-2-thienyl | | |

EXAMPLE 13

Methyl [[[2-Amino-1,6-dihydro-6-oxo-4-[(2-thienylmethyl)amino]-5-pyrimidinyl]amino]thioxomethyl]carbamate (A compound of Scheme 2, Formula II wherein $R_6$ is methyl, n is one, m is zero, $R_4$ and $R_5$ are each hydrogen and Ar is 2-thienyl)

The crude dihydrochloride salt as prepared in Example 12 above (37.2 g, 0 12 mole) was suspended in water (300 ml) and then basified with a mixture of concentrated NH₄OH and 97% hydrazine (3:1) (40 ml) to give the free base which was dried over vacuum over P₂O₅ for 20 hours. Yield 26.1 g (97%) of the base shown as compound of Scheme II, Formula IVb wherein n, m, $R_4$, $R_5$, and Ar are as defined above. This free base was unstable.

A suspension of potassium thiocyanate (18.1 g; 0.186 mole) in acetonitrile (250 ml) was treated with methyl chloroformate (99%) (13.8 ml, 0.177 mole) and the mixture was heated at reflux for one hour, cooled, and then filtered to remove inorganic salts. The bright yellow colored filtrate is stirred overnight at room temperature under nitrogen. Care should be taken so that all of the methylchloroformate has reacted before proceeding. The dry base (26.1 g) was added to the solution of methoxycarbonyl isothiocyanate and the stirring continued for 36 hours at room temperature under nitrogen. The reaction was monitored to completion by TLC (SiO₂; 20% CH₃OH in CHCl₃). The product was filtered off and washed with methanol to give the thiourea derivative, methyl [[[2-amino-1,6-dihydro-6-oxo-4-[(2-thienylmethyl)amino]-5-pyrimidinyl]amino]thioxomethyl]caroamate. Yield 37.4 g (96%), mp 225°-226° C.; (96.6% pure by HPLC).

Alternatively, the nitro or nitrosopyrimidines were catalytically reduced and reacted immediately with ethoxycarbonyl isothiocyanate to give the thiourea derivative.

This material was carried on to the next step without further purification.

EXAMPLE 13A

The procedure described in Example 13 was repeated to prepare the following methyl (or ethyl) [[[2-amino-1,6-dihydro-6-oxo-4-[[(heteroaryl or substituted heteroaryl)methyl]amino]-5-pyrimidinyl]amino]thioxomethyl]carbamate (Table 3) starting from appropriate 2,5-diamino-4-[[(heteroaryl or substituted heteroaryl)methyl]amino]pyrimidin-6-ol, dihydrochloride salt (Table 2).

TABLE 3

| Ar | or Ar | $R_6$ |
|---|---|---|
| 2-Thienyl | (2-thienyl structure) | Et |
| 3-Thienyl | (3-thienyl structure) | $CH_3$ |
| 2-Furanyl | (2-furanyl structure) | $CH_3$ |
| 3-Furanyl | (3-furanyl structure) | $CH_3$ mp 246–249° C. (dec) |
| (2-thienyl)methyl | $-H_2C-$(2-thienyl) | $CH_3$ mp 234–239° C. (dec) |
| 2-Me-3-thienyl | (structure) | $CH_3$ mp 235–237° C. (dec) |
| 5-Me-2-thienyl | (structure) | $CH_3$, mp 227–230° C. (dec) |
| 2-Me-2-thienyl | " | Et |
| 2-Pyridinyl | (pyridinyl structure) | $CH_3$ |
| Benzo[b]thien-2-yl | (structure) | $CH_3$ |
| 2-thiazolyl | (2-thiazolyl structure) | $CH_3$ mp 214–215° C. |
| 4-thiazolyl | (4-thiazolyl structure) | $CH_3$ mp 217–218° C. |
| (3-thienyl)methyl | $-H_2C-$(3-thienyl) | $CH_3$ |
| 5-Me-3-thienyl | (structure) | $CH_3$ |
| 5-Me-2-furanyl | (structure) | $CH_3$ mp 228–229° C. (dec) |
| 4-Me-3-thienyl | (structure) | $CH_3$, Et |
| 4-Me-2-thienyl | (structure) | $CH_3$, Et |

EXAMPLE 14

Methyl [5-amino-7-[(2-thienylmethyl)amino]oxazolo[5,4-d]pyrimidin-2-yl]carbamate (See Scheme 2, Formula III wherein $R_6$ is methyl, n is one, m is zero, $R_4$ and $R_5$ are each hydrogen and Ar is 2-thienyl)

A mixture of the thiourea derivative as prepared in Example 13 (35 g; 0.096 mole) and N,N'-dicyclohexylcarbodiimide (DCC) (59.4 g, 0.288 mole) was suspended in dry DMF (1800 ml) and stirred at room temperature for 24 hours. The course of the reaction was followed by TLC ($SiO_2$; 20%, $CH_3OH$ in $CHCl_3$). The DMF was completely stripped off under vacuum and the residue triturated twice with $CH_2Cl_2$ to give the desired carbamate, methyl [5-amino-7-[(2-thienylmethyl)amino]oxazolo[5,4-d]pyrimidin-2-yl]carbamate. Yield 27.8 g (90%), mp 300° C. Purity 97.6% (HPLC).

This material was carried on to the next step without further purification.

EXAMPLE 14A

The procedure described in Example 14 was repeated to prepare the following methyl (or ethyl) [5-amino-7-[[(heteroaryl or substituted heteroaryl)methyl]amino]oxazolo[5,4-d]pyrimidin-2-yl]carbamate (Table 4) starting from appropriate methyl (or ethyl) [[[2-amino-1,6-dihydro-6-oxo-4-[[(heteroaryl or substituted heteroaryl)methyl]amino]-5-pyrimidinyl]amino]thioxomethyl]carbamate (Table 3).

TABLE 4

| Ar | or Ar | $R_6$ |
|---|---|---|
| 2-Thienyl | | Et |
| 3-Thienyl | | $CH_3$ |
| 2-Furanyl | | $CH_3$ |
| 3-Furanyl | | $CH_3$ mp 288–291° C. (dec) |
| (2-thienyl)methyl | | $CH_3$ mp >270° C. (dec) |
| 2-Me-3-thienyl | | $CH_3$ mp >270° C. (dec) |
| 5-Me-2-thienyl | | $CH_3$, Et p >250° C. (dec) |
| 2-Pyridinyl | | $CH_3$ |
| Benzo[b]thien-2-yl | | $CH_3$ |
| 2-thiazolyl | | $CH_3$ |
| 4-thiazolyl | | $CH_3$ |
| (3-thienyl)methyl | | $CH_3$ |
| 5-Me-3-thienyl | | $CH_3$ |
| 5-Me-2-furanyl | | $CH_3$ |
| 5-Me-2-thienyl | | $CH_3$, Et |
| 5-Me-3-thienyl | | $CH_3$ |
| 4-Me-2-thienyl | | Et mp >260° C. (dec) |

EXAMPLE 15

Methyl [2-amino-6,9-dihydro-6-oxo-9-(2-thienylmethyl-1H-purin-8-yl]carbamate (See Scheme 2, Formula I wherein $R_3$ is $NHCOOR_6$ Wherein $R_6$ is methyl, n is one, m is zero, $R_4$ and $R_5$ are each hydrogen and Ar is 2-thienyl)

A mixture of the oxazolocarbamate as prepared in Example 14 (25 g; 0.078 mole) and anhydrous $K_2CO_3$ was suspended in anhydrous methanol and heated to reflux for eight hours. The course of the reaction is being followed by the TLC system mentioned above. The reaction mixture was then evaporated to dryness under reduced pressure and the residue dissolved in ammonium chloride solution (16.8 g; 0.312 mole in 200 ml of water). The resulting precipitate was collected and dried giving 24.39 g of the methyl[2-amino-6,9-dihydro-6-oxo-9-(2-thienylmethyl)-1H-pyrin-8-yl]carbamate, sometimes contaminated with the 8-amino compound, i.e., in this example, 89.58% carbamate and 9.54% 8-amino compound, 8-amino-9[(2-thienyl)methyl]guanine of Formula I wherein R3 is NH2.

This material was carried on to the next step without further purification.

EXAMPLE 15A

The procedure described in Example 15 was repeated to prepare the following methyl (or ethyl) [2-amino-6,9-dihydro-6-oxo-9-[(heteroaryl or substituted heteroaryl)-methyl-1H-purin-8-yl]carbamate (Table 5) starting from appropriate methyl (or ethyl) [5-amino-7-[[(heteroaryl or substituted heteroaryl)methyl]amino]oxazolo[5,4-d]pyrimidin-2-yl]carbamate (Table 4).

TABLE 5

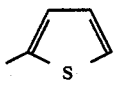

| Ar | or Ar | R6 |
|---|---|---|
| 2-Thienyl | 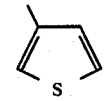 | Et, mp >250° C. (dec) |
| 3-Thienyl | 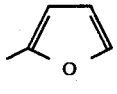 | CH3 |
| 2-Furanyl |  | CH3 mp >300° C. (dec) |
| 3-Furanyl | 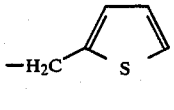 | CH3 mp >270° C. (dec) |
| (2-thienyl)methyl | 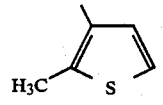 | CH3 |
| 2-Me-3-thienyl | 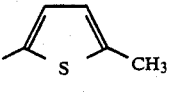 | CH3 |
| 5-Me-2-thienyl | 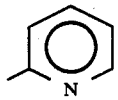 | CH3, Et mp >250° C. (dec) |
| 2-Pyridinyl | 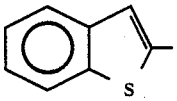 | CH3 |
| Benzo[b]thien-2-yl | 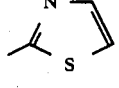 | CH3 |
| 2-thiazolyl | 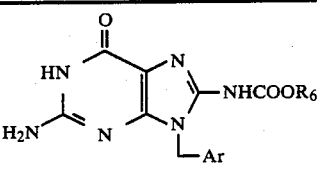 | CH3 |

TABLE 5-continued

| Ar | or Ar | R6 |
|---|---|---|
| 4-thiazolyl | 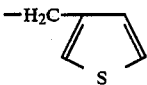 | CH3 |
| (3-thienyl)methyl | 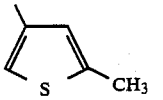 | CH3 |
| 5-Me-3-thienyl | 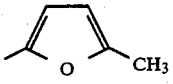 | CH3 |
| 5-Me-2-furanyl | 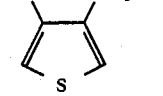 | CH3 mp >250° C. (dec) |
| 4-Me-3-thienyl | 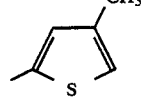 | CH3, Et |
| 4-Me-2-thienyl | (same structure) | CH3, Et |

EXAMPLE 16

8-Amino-9-[(2-thienyl)methyl]guanine (See Scheme 2 Formula I Wherein R3 is NH2, n is one, m is zero, R4 and R5 are each hydrogen and Ar is 2-thienyl)

The crude carbamate as prepared in Example 15 (89.5% the carbamate plus 9.5% the 8-amino compound (20.39 g; 0.064 mole) from the previous reaction is suspended in isopropanol (125 ml) and 1N HCl (125 ml; 0.125 mole) and the mixture heated at reflux for ~20 hours (the reaction is monitored by TLC (SiO2:20% MeOH in CHCl3; CH3CN:HOAc:H2O 8:1:1)), when a clear solution is formed. On cooling the product crystallizes out from the solution as the hydrochloride salt of 8-amino-9[(2-thienyl)methyl]guanine. Yield 15.1 g (76%). Purity 98% by HPLC, mp 219°-222° C. (dec).

The hydrolysis was also carried out in 10% methanolic sodium hydroxide solution under reflux temperature, followed by neutralization and recrystallization from appropriate solvent.

EXAMPLE 16A

The procedure described in Example 16 was repeated to prepare the following 8-amino-9[(heteroaryl or substituted heteroaryl)methyl]guanines (Table 6) starting from appropriate methyl (or ethyl) [2-amino-6,9-dihydro-6-oxo-9-[(heteroaryl or substituted heteroaryl)-methyl-1H-purin-8-yl]carbamate (Table 5).
TABLE 6
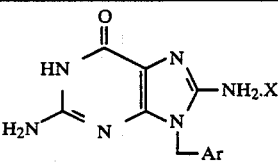
| Ar | or Ar | X | mp °C. |
|---|---|---|---|
| 2-Furanyl | 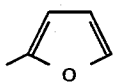 | HCl | 253–7 |
| a. 3-Thienyl |  | HCl.H₂O | 275–8 (d) |
| b. 3-Furanyl |  | HCl | 293–4 (d) |
| c. (2-thienyl)methy | 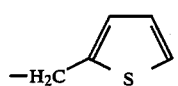 | HCl.H₂O | 153–5 (d) |
| d. 2-Me-3-thienyl | 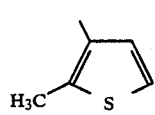 | HCl | 266–8 (d) |
| e. 5-Me-2-thienyl | 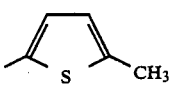 | HCl.0.25 H₂O | >260 |
| f. 2-Pyridinyl | 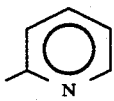 | 1.5 HCl.0.25 H₂O | 270–2 (d) |
| g. Benzo[b]thien-2-yl | 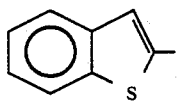 | 0.25 H₂O | >300 (d) |
| h. 2-thiazolyl | 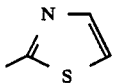 | 1.2 HCl 1.2 H₂O | >250 |
| i. 4-thiazolyl | 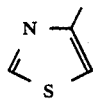 | 1.1 HCl 0.3 H₂O | >250 |
| j. (3-thienyl)methyl | 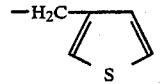 | 0.9 HCl.H₂O | 177–83 (d) |
| k. 5-Me-3-thienyl | 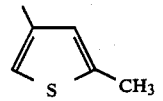 | HCl.0.5 H₂O | 212–5 (d) |

TABLE 6-continued

[Structure: purine-like core with HN, C=O, H₂N-C(=N)-N, and imidazole ring bearing NH₂·X and N-Ar substituents]

| Ar | or Ar | X | mp °C. |
|---|---|---|---|
| l. 5-Me-2-furanyl | [furan with CH₃ at 5-position] | HCl·1.15 H₂O | 212–4 (d) |
| m. 4-Me-3-thienyl | [thiophene with CH₃ groups] | 0.9 HCl 1.25 H₂O | >240 (d) |
| n. 4-Me-2-thienyl | [thiophene with CH₃ at 4-position] | | |

EXAMPLE 17

2,8-Diamino-1,9-dihydro-9-(2-thienylmethyl-6H-purine-6-thione

A mixture of P₂S₅ (2.4 g; 10.95 mmol), pyridine (30 ml) and 8-amino-9[(2-thienyl)methyl]guanine (1.5 g; 4.87 mmol) was heated under reflux for 4.5 hours and then poured into 200 ml of boiling water and boiled for one hour. The mixture was allowed to stand at room temperature overnight. The precipitated solid was collected, dissolved in 1N NaOH, treated with activated charcoal, filtered, and then acidified with glacial acetic acid to pH 5.4. The precipitated solid was collected, dissolved in 1N HCl, treated with activated charcoal, filtered, and neutralized with NH₄OH to pH 7.07 to give 542 mg of the desired product, mp>300° C.

EXAMPLE 17A

The procedure described in Example 17 was repeated to prepare the following 2,8-diamino-1,9-dihydro-9-[(heteroaryl or substituted heteroaryl)methyl]-6H-purin-6-thione, starting from appropriate 8-amino-9[(heteroaryl or substituted heteroaryl)alkyl]guanine.

2,8-Diamino-1,9-dihydro-9-(3-thienylmethyl)-6H-purine-6-thione, 0.5 H₂O, mp 275° C. (dec).

2,8-Diamino-1,9-dihydro-9-[2-(2-thienyl)ethyl]-6H-purine-6-thione, 0.25 H₂O, mp >260° C. (dec).

EXAMPLE 18

2-Amino-7,9-dihydro-9-(2-thienylmethyl)-1H-purine-6,8-dione

A mixture of 8-bromo-9-[(2-thienyl)methyl]guanine (see Example 5) (3.12 g; 9.56 mmol), acetic anhydride (75 ml), glacial acetic acid (75 ml) and anhydrous sodium acetate (14.9 g; 0.1816 mol) was heated to reflux for 20 hours. The dark solution which formed was then evaporated to dryness under reduced pressure. The residue was dissolved in aqueous methylamine (150 ml), stirred at room temperature for 48 hours and then heated to reflux for 2.5 hours. The methylamine was distilled off under reduced pressure and the residue was recrystallized from boiling methanol-water mixture to give 1.23 g of the analytical product, mp >300° C.

EXAMPLE 19

2-Amino-1,7,8,9-tetrahyiro-9-(2-thienylmethyl)-8-thioxo-6H-purin-6-one

A mixture of 8-bromo-9-[(2-thienyl)methyl]guanine (see Example 5) (2.0 g; 6.13 mmol), DMF (250 ml), and thiourea (0.93 g; 12.26 mmol) was heated under reflux for 20 hours and then the solvent was evaporated to dryness under reduced pressure. The residue was dissolved in 1N NaOH, treated with charcoal, filtered, and acidified with glacial AcOH to give a pale yellow solid. Analytical sample was prepared by repeating the purification process, yield 709 mg; mp >280° C.

EXAMPLE 20

N,N'-[6,9-dihydro-6-oxo-9-(2-thienylmethyl)-1H-purin-2,8-di-yl]bis acetamide

A mixture of 8-amino-9-[(2-thianyl)methyl]guanine (0.5 g; 1.88 mmol), DMF (10 ml), pyridine (5 ml), and acetic anhydride (5 ml) was stirred at room temperature for 36 hours. The mixture was diluted with ether (50 ml) and filtered to give analytically pure product, mp 243°–4° C.

STARTING MATERIALS

Starting materials are prepared as follows using a known procedure or following a procedure analogous to that known in the art.

5-Methyl-2-thienylmethylamine, H. Hartough, et al, J. Am. Chem. Soc., 1948, 70:4018.

Benzo[b]thiophen-2-yl-methylamine, D. Shirley, et al, J. Am. Chem. Soc., 1952, 74:664.

3-Methyl-2-thienylmethylamine, H. Hartough, et al, J. Am. Chem. Soc., 1948, 70:4018.

Benzo[b]thiophen-3-yl-methylamine was prepared by Gabriel Synthesis from the corresponding chlorocompound (W. King, et al, J. Org. Chem., 1948, 13:635).

2-Methyl-3-thienylmethylamine was prepared by lithium aluminum hydride (LAH) reduction of the corresponding nitrile (M. Janda, et al, Coll. Czech. Comm., 1974, 39:959).

2-(2-thienyl)ethylamine and 2-(3-thienyl)ethylamine were prepared by the lit. method of W. Hertz, et al, in J. Am. Chem. Soc., 1951, 73:351.

2-Methyl-4-thienyl methylamine was prepared by LAH reduction of 2-methyl-4-cyano-thiophene which was prepared from the corresponding 4-bromo compound (Y. Goldfarb, et al, Zh. Obs. Khim. 1964, 34:969) and CuCN.

3-Methyl-4-thienylmethylamine was similarly prepared as follows:

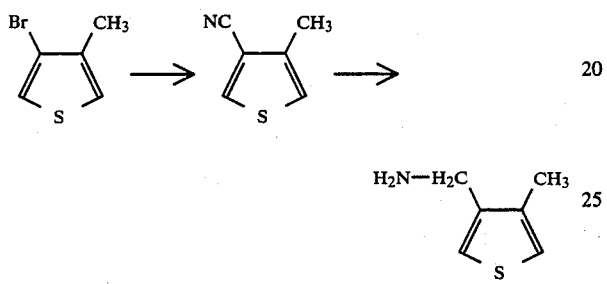

4-Methyl-2-thienylmethylamine was prepared by LAH reduction of the corresponding aldoxime.

2- and 4- Thiazolylmethyl amines were prepared according to the literature procedures (R. G. Jones, et al, J. Am. Chem. Soc., 1950, 72:4526).

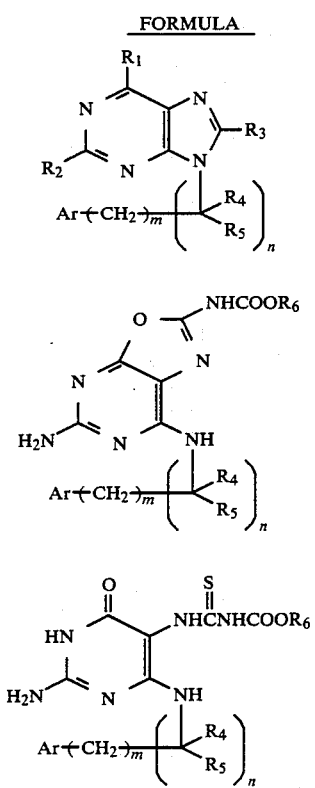

We claim:

1. A compound of the formula:

Wherein $R_6$ is alkyl of one to four carbon atoms, aryl wherein aryl is unsubstituted phenyl or phenyl substituted by halogen, alkyl or one to four carbon atoms, hydroxy, alkoxy of one to four carbon atoms or trifluoromethyl, or arylalkyl wherein aryl is as defined above and alkyl is a carbon chain of up to four carbon atoms; n is zero or one; m is zero, one, two, or three, with the proviso that m or n is at least one; $R_4$ and $R_5$ are each independently hydrogen, alkyl of one to four carbon atoms, aryl is as defined above, arylalkyl is as defined above, or cycloalkyl of three to six carbon atoms, hydroxy, alkyl of one to four carbon atoms and Ar is heteroaryl wherein the heteroaryl is 2- or 3-furanyl, 2- or 3-thienyl, 2-, 3-, or 4-pyridinyl which heteroaryl is unsubstituted or substituted by alkyl of one to four carbons, alkoxy of one to four carbon atoms, —C≡C—C═C— attached to adjacent carbons so as to form a benzo radical, or halogen.

2. A compound according to claim 1 which is methyl[5-amino-7-[(2-thienylmethyl)amino]oxazolo[5,4-d]pyrimidin-2-yl]carbamate.

3. A compound according to claim 1 which is ethyl[5-amino-7-[(2-thienylmethyl)amino]oxazolo[5,4-d]pyrimidin-2-yl]carbamate.

4. A compound according to claim 1 which is methyl[5-amino-7-[(3-thienylmethyl)amino]oxazolo[5,4-d]pyrimidin-2-yl]carbamate.

5. A compound according to claim 1 which is methyl[5-amino-7-[(2-furanylmethyl)amino]oxazolo[5,4-d]pyrimidin-2-yl]carbamate.

6. A compound according to claim 1 which is methyl[5-amino-7-[(3-furanylmethyl)amino]oxazolo[5,4-d]pyrimidin-2-yl]carbamate.

7. A compound according to claim 1 which is methyl[5-amino-7-[(2-thienylethyl)amino]oxazolo[5,4-d]pyrimidin-2-yl]carbamate.

8. A compound according to claim 1 which is methyl[5-amino-7-[(3-(2-methylthienyl)methyl)amino]oxazolo [5,4d]pyrimidin-2-yl]carbamate.

9. A compound according to claim 1 which is methyl[5-amino-7-[(2-(5-methylthienyl)methyl)amino]oxazolo [5,4d]pyrimidin-2-yl]carbamate.

10. A compound according to claim 1 which is methyl[5-amino-7-[(2-pyridinylmethyl)amino]oxazolo[5,4d]pyrimidin-2-yl]carbamate.

11. A compound according to claim 1 which is methyl[5-amino-7-[((benzo[b]thien-2-yl)methyl)amino[oxazolo [5,4d]pyrimidin-2-yl]carbamate.

12. A compound according to claim 1 which is methyl[5-amino-7-[(2-thiazolylmethyl)amino]oxazolo[5,4d]pyrimidin-2-yl]carbamate.

13. A compound according to claim 1 which is methyl[5-amino-7[(4-thiazolylmethyl)amino]oxazolo[5,4d]pyrimidin-2-yl]carbamate.

14. A compound according to claim 1 which is methyl[5-amino-7-[(3-thienylethyl)amino]oxazolo[5,4d]pyrimidin-2-yl]carbamate.

15. A compound according to claim 1 which is methyl[5-amino-7-[(3-(5-methylthienyl)methyl)amino]oxazolo [5,4d]pyrimidin-2-yl]carbamate.

16. A compound according to claim 1 which is methyl[5-amino-7-[(2-(5-methylfuranyl)methyl)amino]oxazolo [5,4d]pyrimidin-2-yl]carbamate.

17. A compound according to claim 1 which is ethyl[5-amino-7-[(2-(5-methylthienyl)methyl)amino]oxazolo [5,4d]pyrimidin-2-yl]carbamate.

18. A compound according to claim 1 which is ethyl[5-amino-7-[(2-(4-methylthienyl)methyl)amino]oxazolo [5,4d]pyrimidin-2-yl]carbamate.

* * * * *